(12) United States Patent
Cutrer et al.

(10) Patent No.: US 8,157,717 B2
(45) Date of Patent: *Apr. 17, 2012

(54) EXPANDABLE BRACHYTHERAPY DEVICE WITH CONSTANT RADIATION SOURCE SPACING

(75) Inventors: L. Michael Cutrer, Huntington Beach, CA (US); Richard A. Terwilliger, Grants Pass, OR (US); Joe Wong, South Pasadena, CA (US); Fredrick Wintch, Snohomish, WA (US)

(73) Assignee: Portola Medical, Inc., Portola Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/544,101

(22) Filed: Aug. 19, 2009

(65) Prior Publication Data

US 2010/0191034 A1    Jul. 29, 2010

Related U.S. Application Data

(63) Continuation of application No. 12/037,534, filed on Feb. 26, 2008, now abandoned, which is a continuation of application No. 11/737,028, filed on Apr. 18, 2007, now Pat. No. 7,357,770.

(60) Provisional application No. 60/882,391, filed on Dec. 28, 2006, provisional application No. 60/864,288, filed on Nov. 3, 2006.

(51) Int. Cl.
    *A61N 5/00* (2006.01)
(52) U.S. Cl. .......................................................... 600/3
(58) Field of Classification Search .................... 600/1–8
    See application file for complete search history.

(56) References Cited

U.S. PATENT DOCUMENTS

| | | |
|---|---|---|
| 5,836,868 A | 11/1998 | Ressemann et al. |
| 5,863,284 A | 1/1999 | Klein |
| 5,938,582 A | 8/1999 | Ciamacco et al. |
| 6,013,019 A * | 1/2000 | Fischell et al. .............. 600/3 |
| 6,217,585 B1 | 4/2001 | Houser et al. |
| 6,413,204 B1 | 7/2002 | Winkler et al. |
| 6,652,548 B2 | 11/2003 | Evans et al. |
| 7,357,770 B1 | 4/2008 | Cutrer et al. |
| 2005/0080313 A1 | 4/2005 | Stewart et al. |
| 2005/0182286 A1 | 8/2005 | Lubock |
| 2006/0100475 A1 | 5/2006 | White et al. |
| 2007/0106108 A1 | 5/2007 | Hermann et al. |
| 2008/0161633 A1 | 7/2008 | Cutrer et al. |

FOREIGN PATENT DOCUMENTS

WO    2008083306 A2    7/2008

OTHER PUBLICATIONS

International Search Report and Written Opinion of the International Searching Authority (ISA/US), mailed Nov. 3, 2008, for PCT Application No. PCT/US07/89092, filed Dec. 28, 2007 (Publication No. WO 2008-083306, published Jul. 10, 2008).

Office Action, dated Feb. 20, 2009, for U.S. Appl. No. 12/037,535, filed Feb. 26, 2008.

* cited by examiner

*Primary Examiner* — Samuel Gilbert

(74) *Attorney, Agent, or Firm* — Locke Lord LLP

(57) ABSTRACT

A brachytherapy device may include an expandable outer cage, an expandable inner cage positioned within the outer cage and configured to receive radioactive material at its perimeter, and a movable actuator configured to cause the outer and inner cages to expand simultaneously in response to movement of the actuator between certain positions while maintaining a substantially constant separation distance between the outer and inner cages.

20 Claims, 3 Drawing Sheets

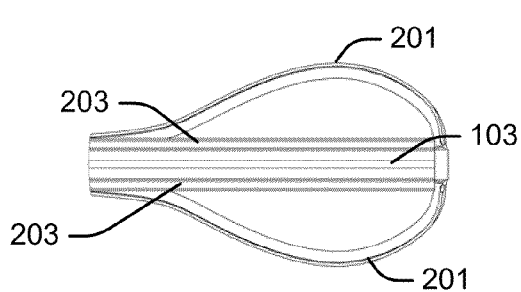
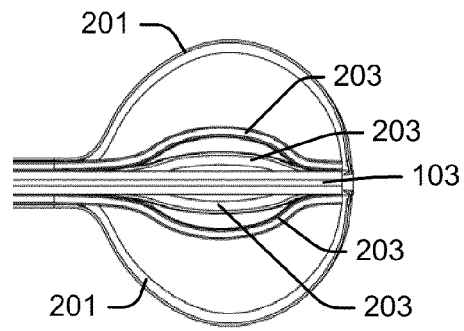
Fig. 3
Fig. 5
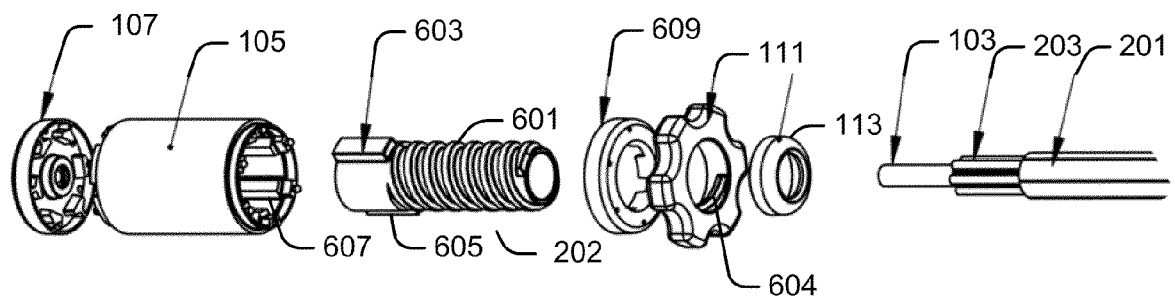
FIG. 6
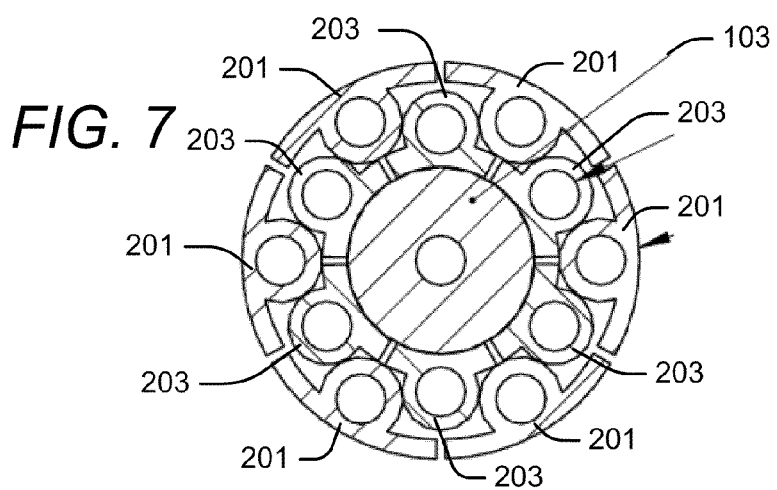
FIG. 7

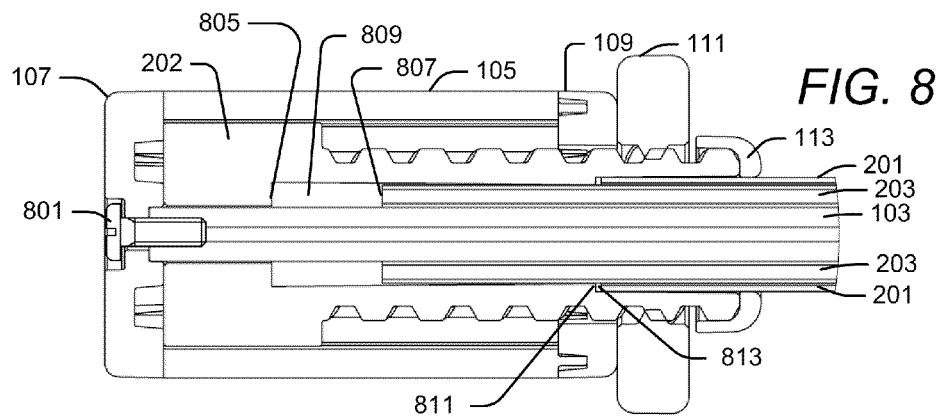
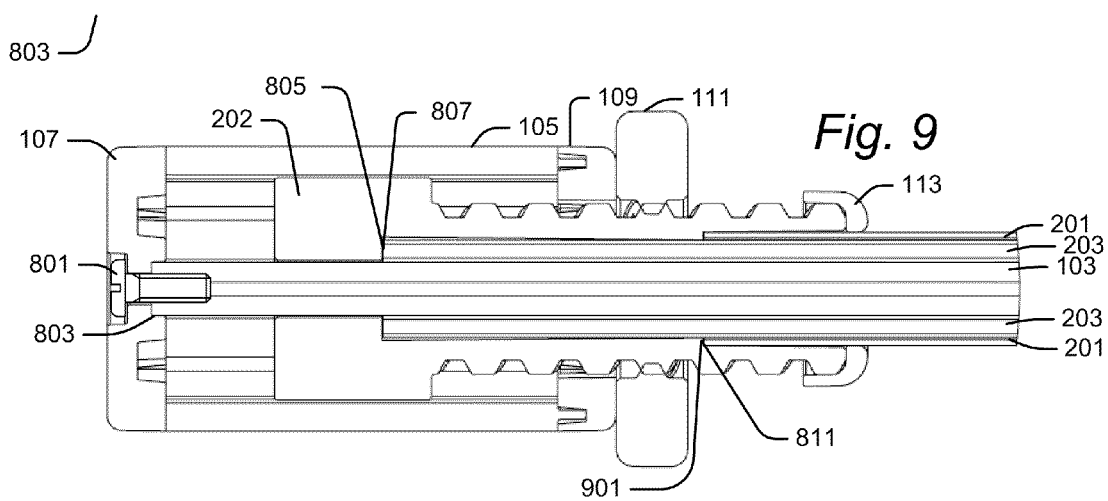
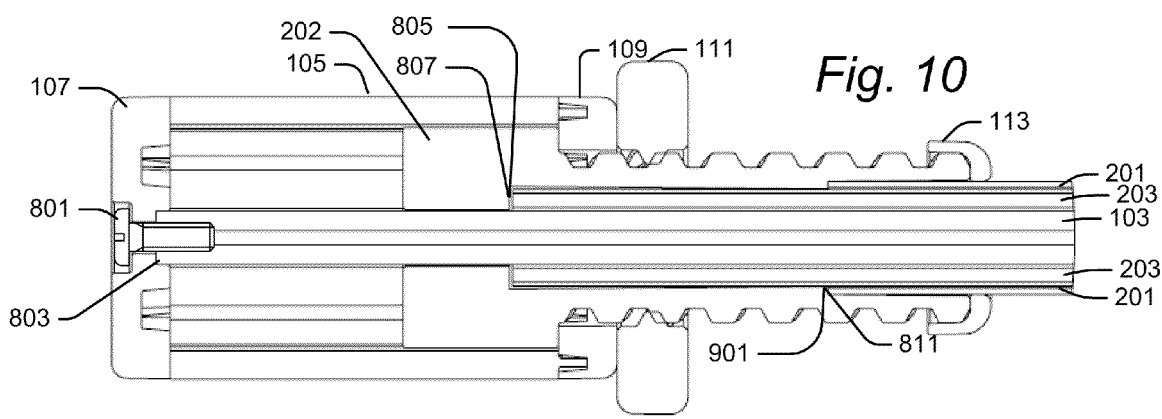

EXPANDABLE BRACHYTHERAPY DEVICE WITH CONSTANT RADIATION SOURCE SPACING

CROSS-REFERENCE TO RELATED APPLICATION(S)

This application is a continuation of U.S. patent application Ser. No. 12/037,534, filed Feb. 26, 2008, now abandoned, entitled "EXPANDABLE BRACHYTHERAPY DEVICE WITH CONSTANT RADIATION SOURCE SPACING," which is a continuation of U.S. patent application Ser. No. 11/737,028, filed Apr. 18, 2007, (now U.S. Pat. No. 7,357,770 B1, issued Apr. 15, 2008), entitled "EXPANDABLE BRACHYTHERAPY DEVICE WITH CONSTANT RADIATION SOURCE SPACING," which is based upon and claims the benefit of U.S. Provisional Patent Application Ser. No. 60/882,391, entitled "EXPANDABLE BRACHYTHERAPY DEVICE WITH CONSTANT RADIATION SOURCE SPACING," filed Dec. 28, 2006. The entire content of all three of these applications and patent is incorporated herein by reference.

This application is also related to U.S. Provisional Patent Application Ser. No. 60/864,288, entitled "BRACHYTHERAPY DEVICE HAVING SEED TUBES WITH INDIVIDUALLY-SETTABLE TISSUE SPACINGS," filed Nov. 3, 2006. This application is also related to U.S. patent application Ser. Nos. 11/305,437, entitled "BRACHYTHERAPY APPARATUS," filed Dec. 16, 2005, now abandoned, and 11/379,739, entitled "BRACHYTHERAPY APPARATUS FOR ASYMMETRICAL CAVITIES," filed Apr. 21, 2006, now abandoned. The entire content of all three of these applications is incorporated herein by reference.

BACKGROUND

1. Field

This application relates to brachytherapy.

2. Description of Related Art

Brachytherapy applies radiation to tissue by placing the source of radiation close to the tissue. Oftentimes, a high dose of radiation is needed. However, it may be difficult to apply a high dose to areas in need of treatment using brachytherapy, without also causing damage to healthy tissue in the vicinity.

One approach to addressing this difficulty is to utilize seed tubes with individually-settable tissue spacings, as described in U.S. Provisional Application Ser. No. 60/864,288, entitled "BRACHYTHERAPY DEVICE HAVING SEED TUBES WITH INDIVIDUALLY-SETTABLE TISSUE SPACINGS," filed Nov. 3, 2006. The technician may individually set the separation distance between each seed tube that carries a radiation seed and the wall of the cavity in which it is placed.

Expertise may be required to ascertain and set the desired spacings in such a device. The use of different spacings, moreover, may complicate the process of creating and implementing an effective treatment regimen.

SUMMARY

A brachytherapy device may include an expandable outer cage, an expandable inner cage positioned within the outer cage and configured to receive radioactive material at its perimeter, and a movable actuator configured to cause the outer and inner cages to expand simultaneously in response to movement of the actuator between certain positions while maintaining a substantially constant separation distance between the outer and inner cages.

The movable actuator may be configured to cause the outer cage to expand but not the inner cage during movement of the actuator between certain other positions.

The movable actuator may be configured to cause the outer and inner cages to expand in a direction perpendicular to the movement of the actuator.

The brachytherapy device may include a ring that is rotatable about an axis and that is configured to cause the movable actuator to traverse the axis when the ring is rotated. The movable actuator and the rotatable ring may have threads that mesh.

The brachytherapy device may include a handle in which the movable actuator moves. The brachytherapy device may include a rod running through the outer and inner cages that is attached to the handle at a distal end.

The outer and inner cages may each include a plurality of tubes. Each of the tubes and the rod may have a proximal end. The proximal end of all of the tubes and the rod may be affixed to one another. Each of the tubes may have a distal end and the actuator may be configured to engage the distal ends of the tubes. The actuator may be configured to apply longitudinal compressive force to the distal ends of the tubes. The outer and inner cages may be configured to collapse into a rod-like shape when the distal ends of the tubes are not engaged by the actuator.

The inner cage may include hollow tubes, each of which may be configured to receive radioactive material at different locations therein.

A brachytherapy device may include a plurality of flexible outer tubes, each having a first length and a distal end. The device may include a plurality of flexible inner tubes positioned within a volume defined by the outer tubes, each having a second length different from the first length, each being configured to receive radioactive material, and each having a distal end. The device may include a movable actuator configured to engage the distal ends of the outer and the inner tubes.

The distal ends of the outer tubes may lie in a first plane and the distal ends of the inner tubes may lie in a second plane. The first and the second planes may be parallel and separated from one another.

A brachytherapy device may include an expandable outer cage, an expandable inner cage positioned within the outer cage and configured to receive radioactive material at its perimeter, and a rotatable actuation mechanism configured to cause the outer and inner cages to expand in response to rotation of the rotatable actuator between certain positions.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. When the same numeral appears in different drawings, it is intended to refer to the same or like components or steps.

FIG. 3 illustrates the expanded outer cage of the brachytherapy device illustrated in FIG. 2 and an inner cage that is still fully collapsed.

FIG. 5 illustrates the expanded outer and inner cages of the brachytherapy device illustrated in FIG. 4.

FIG. 6 is an exploded view of components in the brachytherapy device illustrated in FIGS. 1-5.

FIG. 7 is a cross-section of the tubes illustrated in FIG. 1 in a collapsed state.

FIG. 8 is a cross-section of the handle of the brachytherapy device illustrated in FIG. 1 while in the position shown in FIG. 1.

FIG. 9 is a cross-section of the handle of the brachytherapy device illustrated in FIG. 1 while in the position shown in FIG. 2.

FIG. 10 is a cross-section of the handle of the brachytherapy device illustrated in FIG. 1 while in the position shown in FIG. 4.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation.

Brachytherapy devices may be used to treat cancerous tissue. Examples of such devices and ways in which they may be used are set forth in U.S. Provisional Patent Application 60/864,288, entitled "BRACHYTHERAPY DEVICE HAVING SEED TUBES WITH INDIVIDUALLY-SETTABLE TISSUE SPACINGS," filed Nov. 3, 2006, the entire content of which is incorporated herein by reference. Except for differences described in this provisional application, the brachytherapy devices and associated apparatus that are described in the aforementioned provisional patent application, and the ways in which they may be used, may be used in whole or in part in connection with the devices that are described in this application.

Figure 1:
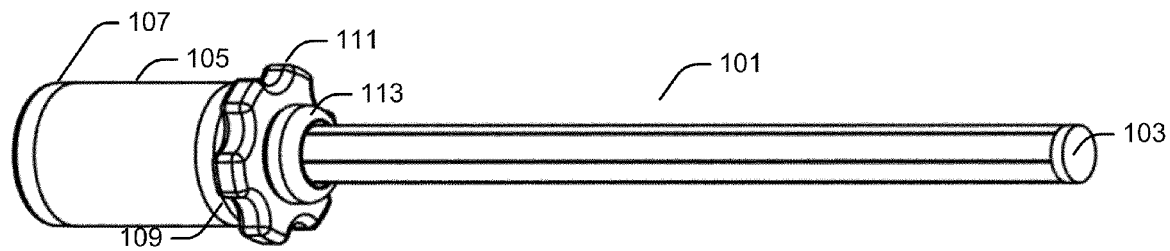
FIG. 1 illustrates a brachytherapy device in a fully collapsed position.

FIG. 1 illustrates a brachytherapy device in a fully collapsed position. As shown in FIG. 1, the brachytherapy device may include tubes 101 positioned around a central rod 103 and attached to a handle 105 that may include a handle end cap 107 and a handle front cap 109. A rotatable ring 111 and an actuator cap 113 may be included. The tubes 101 and the central rod 103 may be attached to one another at a proximal end 115 of the tubes 101 and the central rod 103.

The brachytherapy device illustrated in FIG. 1 may be used in many ways. For example, a tumor may be removed from a breast of a patient. The distance between the surface of the breast and the entryway to the cavity may be measured. A sleeve having a length approximately equal to this measurement may be inserted through an incision in the breast until it reaches the entryway to the cavity. The sleeve may include an external flange that may be sutured to the skin of the breast. Details about illustrative apparatuses and processes that may be used are described in United States Provisional Patent Application entitled "BRACHYTHERAPY DEVICE HAVING SEED TUBES WITH INDIVIDUALLY-SETTABLE TISSUE SPACINGS," Ser. No. 60/864,288, filed Nov. 3, 2006, the entire content of which is incorporated herein by reference.

The proximal end 115 of the collapsed brachytherapy device may be inserted into the sleeve until the proximal end 115 passes through the entryway to the cavity and comes into contact with the opposite wall of the cavity.

Figure 2:
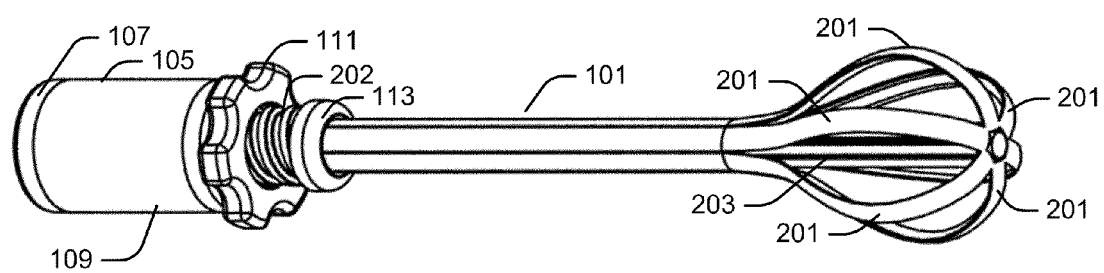
FIG. 2 illustrates the brachytherapy device illustrated in FIG. 1 after an outer cage has been partially expanded.

FIG. 2 illustrates the brachytherapy device illustrated in FIG. 1 after an outer cage has been partially expanded. To expand into this position, the rotatable ring 111 may have been rotated with respect to the handle 105. This may have caused an actuator 202 to traverse the rotational axis of the rotatable ring 111, as illustrated in FIG. 2. The translation of the actuator 202, in turn, may have caused the actuator 202 to have compressed outer tubes 201 of the tubes 101, thus causing them to bow, as illustrated in FIG. 2. Details of mechanisms that may cause this compression are described below in connection with FIGS. 8-10.

As discussed above, the tubes 101 of the brachytherapy device may be within a sleeve that has been inserted into the breast. As also explained above, the tubes 101 may protrude beyond the sleeve at the entryway to the cavity until their proximal end 115 reaches the other wall of the cavity. In this configuration, only the portion of the tubes that lie within the cavity are free to bow. This explains why only the proximal portion of the outer tubes 201 are shown as bowed in FIG. 2.

As partially illustrated in FIG. 2, inner tubes 203 defining an inner cage may be contained within the volume defined by the outer tubes 201 and may remain uncompressed by the actuator 202 at this point and thus in an unbowed and collapsed state.

FIG. 3 illustrates the expanded outer cage of the brachytherapy device illustrated in FIG. 2 and the inner cage that is still fully collapsed.

Figure 4:
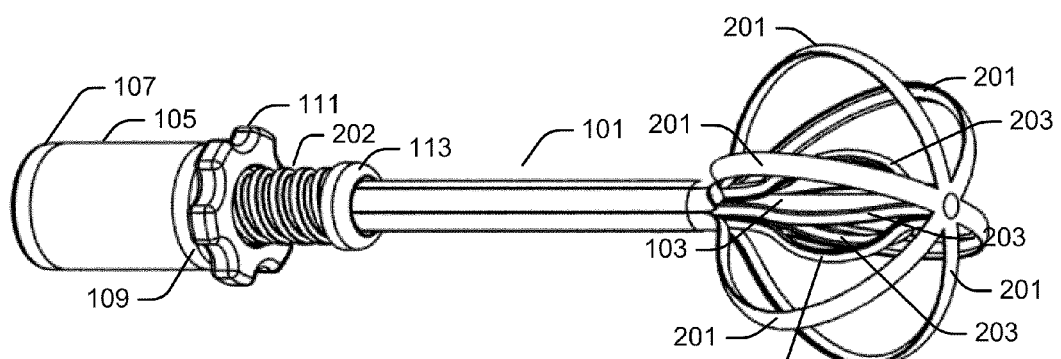
FIG. 4 illustrates the brachytherapy device illustrated in FIG. 1 after both the outer cage and the inner cage have been expanded.

FIG. 4 illustrates the brachytherapy device illustrated in FIG. 1 after both the outer cage and the inner cage have been expanded. To expand into this position, the rotatable ring 111 may have been rotated further. This may have continued to cause the actuator 202 to traverse the rotation axis of the rotatable ring 111, as illustrated in FIG. 4. As the actuator 202 continued to traverse, it may have continued to compress the outer tubes 201, thus causing them to bow further. The actuator 202 may also have begun to compress the inner tubes 203, thus causing the inner tubes 203 to also bow, as also illustrated in FIG. 4. Once the rotatable ring 111 is rotated to a point that causes the actuator 202 to begin to compress the inner tubes 203, the inner tubes may bow in substantial unison with the outer tubes 201. Again, details of mechanisms that may cause this compression are described below in connection with FIGS. 8-10.

FIG. 5 illustrates the expanded outer and inner cages of the brachytherapy device as shown in FIG. 4.

The rotatable ring 111 may continue to be rotated until the cage defined by the outer tubes 201 fills the cavity within the breast to a desired degree, such as until the outer cage substantially fills the cavity.

The degree to which the outer cage defined by the outer tubes 201 is expanded may vary to match different size breast cavities. However, the spacing between the inner tubes 203 and the outer tubes 201 and thus the surface of the cavity may remain substantially constant, notwithstanding these difference in expansion. The phrase "substantially constant" is intended to take into consideration small changes in the separation distance that may occur due to the geometries of the arrangement.

As should now be apparent, both the outer cage and the inner cage may be expanded to needed positions merely by the rotation of a single component, namely in this embodiment, the rotatable ring 111.

FIG. 6 is an exploded view of components of the brachytherapy device illustrated in FIGS. 1-5. As shown in FIG. 6, the actuator 202 may include threads 601 configured to mate with corresponding threads 604 in the rotatable ring 111. The actuator 202 may include tabs 603 and 605 that may engage corresponding slots in the handle 105. For example, the tab 605 may engage a slot 607 in the handle 105. A retaining ring 609 may also be attached to the handle 105 so as to insure that the actuator 202 is retained within the handle 105.

The net effect of the components that have thus-far been described in connection with FIG. 6 may be to cause the actuator 202 to traverse the rotational axis of the rotatable ring 111 as the rotatable ring 111 is rotated. Rotation of the rotatable ring 111 may pull on the threads 601 on the actuator 202, while the tabs 603 and 605 and their corresponding slots in the handle 105 may prevent the actuator 202 from also rotating, thus causing the actuator 202 to traverse the rotation axis of the rotatable ring 111.

As also shown in FIG. 6, the outer tubes 201 may have a length that is shorter than the inner tubes 203. Similarly, the inner tubes 203 may have a length that is shorter than the central rod 103.

FIG. 7 is a cross-section of the tubes illustrated in FIG. 1 in a collapsed state. As shown in FIG. 7, the outer tubes 201 may define an interior volume in which the inner tubes 203 reside. Similarly, the inner tubes 203 may define an interior volume in which the central rod 103 resides. As also illustrated in FIG. 7, each of the inner tubes 203 and each of the outer tubes 201 may be hollow. In an alternate embodiment, one or more of the inner and/or the outer tubes 201 may not be hollow.

FIG. 8 is a cross-section of the handle of the brachytherapy device illustrated in FIG. 1 while in the position shown in FIG. 1. As shown in FIG. 8, a screw 801 may secure a distal end 803 of the central rod 103 to the handle end cap 107.

While in the position shown in FIG. 8, the actuator 202 may not apply any pressure to distal ends 811 of the outer tubes 201 or to distal ends 807 of the inner tubes 203, thus allowing the outer tubes 201 and the inner tubes 203 to be in the completely collapsed position illustrated in FIG. 1.

FIG. 9 is a cross-section of the handle of the brachytherapy device illustrated in FIG. 1 while in the position shown in FIG. 2. In order to have gotten into the position illustrated in FIG. 9, the rotatable ring 111 may have been rotated, thus causing the actuator 202 to have traversed the rotational axis of the rotatable ring 111, as illustrated in FIG. 9. As it began this traverse, an annular surface 901 within the interior of the actuator 202 may have engaged the distal ends 811 of the outer tubes 201, thus applying longitudinal compressive force on the outer tubes 201 with respect to the central rod 103 whose distal end 803 may be attached to the handle end cap 107 by the screw 801. This longitudinal compression may have caused the length of the outer tubes 201 that protrudes beyond the sleeve (see discussion above) to bow, as illustrated in FIGS. 2 and 3.

As illustrated in FIG. 8, the actuator 202 may have a second annular surface 805 on its interior which may initially be longitudinally separated from the distal ends 807 of the inner tubes 203. Thus, longitudinal pressure may not be asserted by the second annular surface 805 against the distal ends 807 of the inner tubes 203 during the initial portion of the traverse of the actuator 202.

Once the rotatable ring 111 is rotated by a certain amount, the gap 809 between the second annular surface 805 and the distal ends 807 of the inner tubes 203 may close, thus causing the second annular surface 805 to engage the distal ends 807 of the inner tubes 203, as illustrated in FIG. 9.

FIG. 10 is a cross-section of the handle of the brachytherapy device illustrated in FIG. 1 while in the position shown in FIG. 4. As the rotatable ring 111 continues to be rotated past the point shown in FIG. 9, the actuator 202 may apply longitudinal compressive force simultaneously to both the outer tubes 201 and the inner tubes 203 by virtue of force being applied by the annular surface 901 to the distal ends of the outer tubes 201 and by the second annular surface 805 to the distal ends 807 of the inner tubes 203. This may cause the outer tubes 201 and the inner tubes 203 to bow in unison. In turn, this may cause the distance between the outer tubes 201 and the inner tubes 203 to remain substantially constant, notwithstanding continued bowing of the outer tubes 201 and the inner tubes 203.

The rotatable ring 111 may continue to be rotated until the cage defined by the outer tubes 201 expands to the desired amount or until the actuator 202 is prevented from traversing any further through the rotational axis of the rotatable ring 111 by the front cap 109.

After the outer tubes 201 have been expanded to the desired or maximum amount, the shaft of the tubes 101 at the entryway to the handle 105 may be clamped, the handle 105 may be detached from the tubes 101 by cutting the tubes 101 between the clamp and the handle 105, and one or more radiation sources, such as one or more radioactive seeds, may be inserted into the hollow interior of one or more of the inner tubes 203 and/or the outer tubes 201 in accordance with a treatment plan. Examples of apparatuses and related processes that may be used in connection with these steps are described in U.S. Provisional Application Ser. No. 60/864, 288, entitled "BRACHYTHERAPY DEVICE HAVING SEED TUBES WITH INDIVIDUALLY-SETTABLE TISSUE SPACINGS," filed Nov. 3, 2006, the entire content of which is incorporated herein by reference.

The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

For example, a fluid barrier, such as an expandable sheath, may be placed around the tubes 101 so as to prevent fluid from filling the cage defined by the outer tubes 201 both before and after they are expanded. The interior of this fluid barrier may be filled with air or fluid from an external source. For example, the central rod 103 may have a lumen through which fluid may be delivered from outside of the breast. The fluid may flow into the interior of the fluid barrier through one or more holes in the proximal end of the central rod 103 (not shown).

Although the annular surfaces 805 and 901 have thus-far been illustrated as being in separate planes, these two surfaces could instead be replaced by a single annual surface. In this embodiment, the differential in the lengths of the outer tubes 201 and the inner tubes 203 may be increased to compensate. Conversely, the lengths of the outer tubes 201 and the inner tubes 203 may be the same, while the annular surfaces 805 and 901 may be separated by a greater distance to compensate.

The amount of the substantially constant spacing between the outer tubes 201 and the inner tubes 203 may be varied by a variety of means. For example, different tube sets may be provided, each with a different distance between the distal ends of the outer tubes 201 and the inner tubes 203. The technician may select the tube set that will provide the desired separation distance. Similarly, different handles may be provided which have different longitudinal spacings between the two annular surfaces 805 and 901. In this event, the technician may instead select the handle that will provide the desired spacing. In a still further embodiment, the longitudinal location of the annular surface 805 and/or the annular surface 901 may be adjustable.

Although certain mechanical designs have been described to effectuate the bowing of the tubes 101, these are only examples. Any other design may be used instead.

Appropriate apparatuses may also be provided to allow the degree of bowing in the inner tubes 203 and/or the outer tubes 201 to be individually adjusted either before, during or after these tubes are bowed in unison as a result of the rotation of the rotatable ring 111. U.S. Provisional Patent Application Ser. No. 60/864,288, entitled "BRACHYTHERAPY DEVICE HAVING SEED TUBES WITH INDIVIDUALLY-SETTABLE TISSUE SPACINGS," filed Nov. 3, 2006, sets forth examples of apparatuses that may be used to effectuate such individual adjustments. Any of the apparatuses and methods shown in U.S. patent application Ser. No. 11/305,437, entitled "BRACHYTHERAPY APPARATUS," filed Dec. 16, 2005, and Ser. No. 11/379,739, entitled "BRACHYTHERAPY APPARATUS FOR ASYMMETRICAL CAVITIES," filed Apr. 21, 2006, may be used in addition or instead.

Although having thus-far been describe for use in connection with treating a breast, the brachytherapy devices and methods that have been described may also be used to treat other areas of a body, such as the brain or prostrate.

The phrase "means for" when used in a claim embraces the corresponding structures and materials that have been described and their equivalents. Similarly, the phrase "step for" when used in a claim embraces the corresponding acts that have been described and their equivalents. The absence of these phrases means that the claim is not limited to any of the corresponding structures, materials, or acts or to their equivalents.

Nothing that has been stated or illustrated is intended to cause a dedication of any component, step, feature, object, benefit, advantage, or equivalent to the public, regardless of whether it is recited in the claims.

In short, the scope of protection is limited solely by the claims that now follow. That scope is intended to be as broad as is reasonably consistent with the language that is used in the claims and to encompass all structural and functional equivalents.

The invention claimed is:

1. A brachytherapy device comprising:
an expandable outer cage formed with a plurality of arms when expanded includes open space between the arms;
an expandable inner cage positioned within the outer cage and at least one of the arms having a lumen adapted to receive radioactive material at its perimeter; and
a movable actuator configured to cause the outer and inner cages to expand simultaneously in response to movement of the actuator between certain positions while maintaining a substantially constant separation distance between the outer and inner cages.

2. The brachytherapy device of claim 1 wherein the separation distance is other than substantially zero.

3. The brachytherapy device of claim 1 wherein the movable actuator is configured to cause the outer cage to expand, but not the inner cage, during movement of the actuator between certain other positions.

4. The brachytherapy device of claim 1 wherein the movable actuator is configured to cause the outer and inner cages to expand in a direction perpendicular to the movement of the actuator.

5. The brachytherapy device of claim 1 further comprising a ring that is rotatable about an axis and that is configured to cause the movable actuator to traverse the axis when the ring is rotated.

6. The brachytherapy device of claim 1 wherein the movable actuator and the rotatable ring have threads that mesh.

7. The brachytherapy device of claim 1 wherein the outer and inner cages are configured to collapse into a rod-like shape having a substantially uniform diameter.

8. The brachytherapy device of claim 1 wherein the inner cage includes a plurality of hollow tubes, each configured to receive radioactive material.

9. The brachytherapy device of claim 1 wherein the inner cage includes a plurality of tubes and the actuator is configured to engage ends of the tubes.

10. The brachytherapy device of claim 9 wherein the outer and inner cages are configured to collapse into a rod-like shape having a substantially uniform diameter when the ends of the tubes are not engaged by the actuator.

11. The brachytherapy device of claim 9 wherein the actuator is configured to apply longitudinal compressive force to the ends of the tubes.

12. A brachytherapy device comprising:
an expandable outer compartment;
an expandable inner compartment positioned within the outer compartment and configured to support radioactive material at its perimeter; and
a movable actuator configured to cause the outer and inner compartments to expand simultaneously in response to movement of the actuator between certain positions while maintaining a substantially constant and non-zero separation distance between.

13. The brachytherapy device of claim 12 wherein the outer and inner compartments are configured to collapse into a rod-like shape having a substantially uniform diameter.

14. The brachytherapy device of claim 13 wherein the inner and outer compartments are attached at one end.

15. The brachytherapy device of claim 14 wherein the moveable actuator includes a rod attached at the one end.

16. The brachytherapy device of claim 12 wherein the inner and outer compartments are configured to expand in response to compressive force being applied to the compartments.

17. The brachytherapy device of claim 16 wherein the inner and outer compartments are configured to expand in a direction substantially orthogonal to the direction of the compressive force.

18. The brachytherapy device of claim 12 wherein the movable actuator includes a single component which, upon being moved, is configured to cause both the inner and outer compartments to expand simultaneously.

19. The brachytherapy device of claim 18 wherein the single component is a substantially-circular ring.

20. The brachytherapy device of claim 18 wherein the movement of the single component is rotational movement.

* * * * *